United States Patent
Linderoth et al.

(10) Patent No.: US 11,779,631 B2
(45) Date of Patent: Oct. 10, 2023

(54) CD47 BLOCKADE THERAPY BY HDAC INHIBITORS

(71) Applicant: TRILLIUM THERAPEUTICS ULC, Mississauga (CA)

(72) Inventors: Emma Linderoth, Toronto (CA); Natasja Nielsen Viller, Oakville (CA); Robert Adam Uger, Richmond Hill (CA); Penka Slavcheva Slavova-Petrova, Toronto (CA)

(73) Assignee: Pfizer Inc., New York, NY (US)

( * ) Notice: Subject to any disclaimer, the term of this patent is extended or adjusted under 35 U.S.C. 154(b) by 628 days.

(21) Appl. No.: 16/344,985

(22) PCT Filed: Nov. 1, 2017

(86) PCT No.: PCT/CA2017/051301
§ 371 (c)(1),
(2) Date: Apr. 25, 2019

(87) PCT Pub. No.: WO2018/081898
PCT Pub. Date: May 11, 2018

(65) Prior Publication Data
US 2019/0269756 A1 Sep. 5, 2019

Related U.S. Application Data

(60) Provisional application No. 62/416,968, filed on Nov. 3, 2016.

(51) Int. Cl.
*A61K 38/17* (2006.01)
*A61K 31/395* (2006.01)
*A61K 38/15* (2006.01)
*A61K 39/395* (2006.01)
*A61P 35/00* (2006.01)
*C07K 16/28* (2006.01)
*A61P 35/02* (2006.01)
*C07K 14/705* (2006.01)

(52) U.S. Cl.
CPC ........ *A61K 38/1741* (2013.01); *A61K 31/395* (2013.01); *A61K 38/15* (2013.01); *A61K 38/1709* (2013.01); *A61K 39/395* (2013.01); *A61K 39/39541* (2013.01); *A61P 35/00* (2018.01); *A61P 35/02* (2018.01); *C07K 14/70596* (2013.01); *C07K 16/2803* (2013.01); *C07K 2317/76* (2013.01)

(58) Field of Classification Search
CPC .. A61K 38/1741; A61K 31/395; A61K 38/15; A61K 38/1709; A61K 39/395; A61K 39/39541; A61P 35/00; A61P 35/02; C07K 14/70596; C07K 16/2803; C07K 2317/76
See application file for complete search history.

(56) References Cited

U.S. PATENT DOCUMENTS

| | | | |
|---|---|---|---|
| 6,913,894 B2 | 7/2005 | Buhring et al. | |
| 8,377,448 B2 | 2/2013 | Smith et al. | |
| 8,562,997 B2 | 10/2013 | Jaiswal et al. | |
| 9,650,441 B2 | 5/2017 | Grosveld et al. | |
| 9,803,016 B2 | 10/2017 | Grosveld et al. | |
| 2015/0094518 A1* | 4/2015 | Wu | A61K 9/06 600/1 |
| 2019/0091290 A1* | 3/2019 | Lin | A61K 38/217 |
| 2020/0010544 A1 | 1/2020 | Pogue et al. | |

FOREIGN PATENT DOCUMENTS

| | | |
|---|---|---|
| WO | WO-2010/070047 A1 | 6/2010 |
| WO | WO-2010/083253 A2 | 7/2010 |
| WO | WO-2010/130053 A1 | 11/2010 |
| WO | WO-2012/030886 A1 | 3/2012 |
| WO | WO-2013/056352 A1 | 4/2013 |
| WO | WO-2013/109752 A1 | 7/2013 |
| WO | WO-2014/094122 A1 | 6/2014 |
| WO | WO-2014/123580 A1 | 8/2014 |
| WO | WO-2015/103989 A1 | 7/2015 |
| WO | WO-2016/004875 A1 | 1/2016 |
| WO | WO-2016/022971 A1 | 2/2016 |
| WO | WO-2016/024021 A1 | 2/2016 |
| WO | WO-2016/054555 A2 | 4/2016 |
| WO | WO-2016/081423 A1 | 5/2016 |
| WO | WO-2017/177333 A1 | 10/2017 |
| WO | WO-2017/181033 A1 | 10/2017 |
| WO | WO-2018/081897 A1 | 5/2018 |
| WO | WO-2018/176132 A1 | 10/2018 |
| WO | WO-2018/236904 A1 | 12/2018 |

OTHER PUBLICATIONS

Irandoust et al. Engagement of SIRPα Inhibits Growth and Induces Programmed Cell Death in Acute Myeloid Leukemia Cells. PLOS One 8(1): 1-13, Published: Jan. 8, 2013.*
Zhang et al. (Front. Immunol. 11(18): 1-15, Jan. 2020).*
European Patent Application No. 17868258.9, Extended European Search Report, dated May 25, 2020.
Ververis et al., Histone deacetylase inhibitors (HDACIs): multitargeted anticancer agents, Biologics, 7:47-60 (2013).

(Continued)

*Primary Examiner* — Alana Harris Dent

(74) *Attorney, Agent, or Firm* — Stephen E. Moyer

(57) ABSTRACT

CD47$^+$ disease cells such as cancer cells are treated using a combination of CD47 blockade drug and a histone deacetylase (HDAC) inhibitor. The anti-cancer effect of one drug enhances the anti-cancer effect of the other. Specific combinations include SIRPαFc as CD47 blockade drug, and one of depsipeptide and romidepsin as HDAC inhibitor. These combinations are useful particularly to treat blood cancers including lymphomas, leukemias and myelomas.

Figure 1:
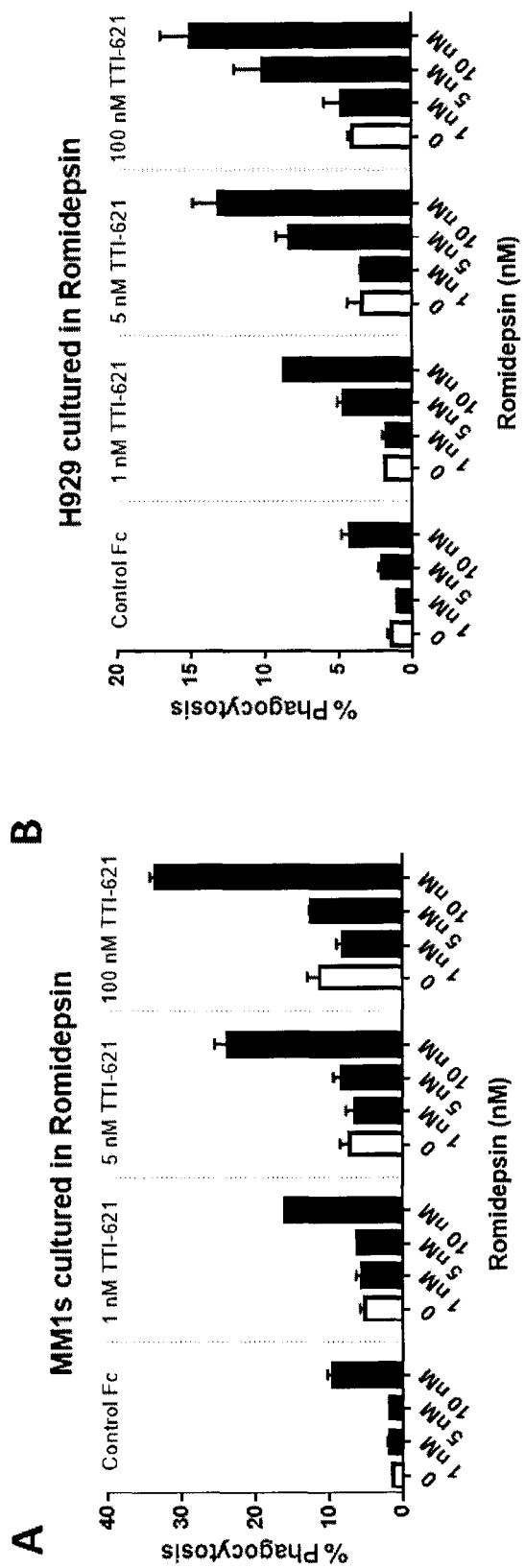

17 Claims, 2 Drawing Sheets
Specification includes a Sequence Listing.

(56) References Cited

OTHER PUBLICATIONS

Izykowska et al., Novel targeted therapies of T cell lymphomas, J. Hematol. Oncol., 3:176 (2020).
International Application No. PCT/CA2017/051301, International Search Report and Written Opinion, dated Feb. 1, 2018.

* cited by examiner

SEQUENCE LISTING

```
<160> NUMBER OF SEQ ID NOS: 16

<210> SEQ ID NO 1
<211> LENGTH: 106
<212> TYPE: PRT
<213> ORGANISM: Homo sapiens

<400> SEQUENCE: 1

Glu Glu Leu Gln Val Ile Gln Pro Asp Lys Ser Val Ser Val Ala Ala
1               5                   10                  15

Gly Glu Ser Ala Ile Leu His Cys Thr Val Thr Ser Leu Ile Pro Val
            20                  25                  30

Gly Pro Ile Gln Trp Phe Arg Gly Ala Gly Pro Ala Arg Glu Leu Ile
        35                  40                  45

Tyr Asn Gln Lys Glu Gly His Phe Pro Arg Val Thr Thr Val Ser Glu
    50                  55                  60

Ser Thr Lys Arg Glu Asn Met Asp Phe Ser Ile Ser Ile Ser Asn Ile
65                  70                  75                  80

Thr Pro Ala Asp Ala Gly Thr Tyr Tyr Cys Val Lys Phe Arg Lys Gly
                85                  90                  95

Ser Pro Asp Thr Glu Phe Lys Ser Gly Ala
            100                 105

<210> SEQ ID NO 2
<211> LENGTH: 118
<212> TYPE: PRT
<213> ORGANISM: Homo sapiens

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115
```

```
<210> SEQ ID NO 3
<211> LENGTH: 227
<212> TYPE: PRT
<213> ORGANISM: Homo sapiens

<400> SEQUENCE: 3
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

```
<210> SEQ ID NO 4
<211> LENGTH: 216
<212> TYPE: PRT
<213> ORGANISM: Homo sapiens

<400> SEQUENCE: 4
```

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

```
Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
        130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 5
<211> LENGTH: 217
<212> TYPE: PRT
<213> ORGANISM: Homo sapiens

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 6
<211> LENGTH: 229
<212> TYPE: PRT
```

<213> ORGANISM: Homo sapiens

<400> SEQUENCE: 6

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 7
<211> LENGTH: 229
<212> TYPE: PRT
<213> ORGANISM: Homo sapiens

<400> SEQUENCE: 7

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro

```
            115                 120                 125
Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 8
<211> LENGTH: 345
<212> TYPE: PRT
<213> ORGANISM: Homo sapiens

<400> SEQUENCE: 8

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255
```

-continued

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
        290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 9
<211> LENGTH: 345
<212> TYPE: PRT
<213> ORGANISM: Homo sapiens

<400> SEQUENCE: 9

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
            290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 10
<211> LENGTH: 347
<212> TYPE: PRT
<213> ORGANISM: Homo sapiens

<400> SEQUENCE: 10

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Pro
        115                 120                 125

Cys Pro Ala Pro Glu Phe Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Arg Leu Thr Val Asp Lys Ser Arg Trp Gln Glu Gly

```
                305                 310                 315                 320
Asn Val Phe Ser Cys Ser Val Met His Glu Ala Leu His Asn His Tyr
                325                 330                 335

Thr Gln Lys Ser Leu Ser Leu Ser Leu Gly Lys
                340                 345

<210> SEQ ID NO 11
<211> LENGTH: 117
<212> TYPE: PRT
<213> ORGANISM: Homo sapiens

<400> SEQUENCE: 11

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro
        115

<210> SEQ ID NO 12
<211> LENGTH: 346
<212> TYPE: PRT
<213> ORGANISM: Homo sapiens

<400> SEQUENCE: 12

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Pro
        115                 120                 125

Cys Pro Ala Pro Pro Val Ala Gly Pro Ser Val Phe Leu Phe Pro Pro
            130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
```

```
                    165                 170                 175
Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
            245                 250                 255

Met Thr Lys Asn Gln Val Ser Leu Thr Cys Leu Val Lys Gly Phe Tyr
        260                 265                 270

Pro Ser Asp Ile Ala Val Glu Trp Glu Ser Asn Gly Gln Pro Glu Asn
    275                 280                 285

Asn Tyr Lys Thr Thr Pro Pro Val Leu Asp Ser Asp Gly Ser Phe Phe
        290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
            325                 330                 335

Gln Lys Ser Leu Ser Leu Ser Leu Gly Lys
        340                 345

<210> SEQ ID NO 13
<211> LENGTH: 118
<212> TYPE: PRT
<213> ORGANISM: Murine

<400> SEQUENCE: 13

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
            85                  90                  95

Ala Arg Ser Leu Ala Gly Asn Ala Met Asp Tyr Trp Gly Gln Gly Thr
            100                 105                 110

Ser Val Thr Val Ser Ser
        115

<210> SEQ ID NO 14
<211> LENGTH: 107
<212> TYPE: PRT
<213> ORGANISM: Murine

<400> SEQUENCE: 14

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
```

```
                    20                  25                  30
Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys
                100                 105

<210> SEQ ID NO 15
<211> LENGTH: 5
<212> TYPE: PRT
<213> ORGANISM: Artificial Sequence
<220> FEATURE:
<223> OTHER INFORMATION: Synthetic construct

<400> SEQUENCE: 15

Gly Gly Gly Gly Ser
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic construct

<400> SEQUENCE: 16

Gly Thr Glu Leu Ser Val Arg Ala Lys Pro Ser
1               5                   10
```

CD47 BLOCKADE THERAPY BY HDAC INHIBITORS

CROSS-REFERENCE

This application claims the benefit under 35 USC § 119(e) from U.S. Provisional patent application Ser. No. 62/416,968, filed Nov. 3, 2016, which is incorporated herein by reference in its entirety.

FIELD

This disclosure relates to methods and uses of a drug that blocks the CD47/SIRPα interaction. More particularly, the disclosure relates to methods and uses that, in combination, are useful for improving cancer therapy.

BACKGROUND

Cancer cells are targeted for destruction by antibodies that bind to cancer cell antigens, and through recruitment and activation of macrophages by way of Fc receptor binding to the Fc portion of that antibody. Binding between CD47 on cancer cells and SIRPα on macrophages transmits a "don't eat me" signal that enables many tumour cells to escape destruction by macrophages. It has been shown that inhibition of the CD47/SIRPα interaction (CD47 blockade) will allow macrophages to "see" and destroy the target CD47$^+$ cancer cell. The use of SIRPα to treat cancer by CD47 blockade is described in WO2010/130053.

*Trillium* Therapeutics' WO2014/094122 describes a protein drug that inhibits the interaction between CD47 and SIRPα. This CD47 blockade drug is a form of human SIRPα that incorporates a particular region of its extracellular domain linked with a particularly useful form of an IgG1-based Fc region. In this form, the SIRPαFc drug shows dramatic effects on the viability of cancer cells that present with a CD47$^+$ phenotype. The effect is seen particularly on acute myelogenous leukemia (AML) cells, and many other types of cancer. A soluble form of SIRP having significantly altered primary structure and potent CD47 binding affinity is described in WO2013/109752.

Other CD47 blockade drugs have been described, and these include various CD47 antibodies (see for instance Stanford's U.S. Pat. No. 8,562,997, and InhibRx' WO2014/123580), each comprising different antigen binding sites but having, in common, the ability to compete with endogenous SIRPα for binding to CD47, to interact with macrophages and, ultimately, to increase CD47$^+$ disease cell depletion. These CD47 antibodies have activities in vivo that are quite different from those intrinsic to drugs that incorporate SIRPα structure. The latter, for instance, display negligible binding to red blood cells whereas the opposite property in CD47 antibodies, and in high affinity SIRPα variants, creates a need for strategies that accommodate a drug "sink" that follows administration.

Still other agents are proposed for use in blocking the CD47/SIRPα axis. These include CD47Fc proteins described in Viral Logic's WO2010/083253, and SIRPα antibodies as described in University Health Network's WO2013/056352, Eberhard's U.S. Pat. No. 6,913,894, and elsewhere.

The CD47 blockade approach in anti-cancer drug development shows great promise. There is a need to provide methods and means for improving the effect of these drugs, and in particular for improving the effect of the CD47 blockade drugs that incorporate CD47-binding forms of SIRPα.

SUMMARY

It is now shown that the anti-cancer effect of CD47 blockade therapy is improved when combined with an agent that inhibits histone deacetylase (HDAC) activity. More particularly, significant improvement in cancer cell vitality and/or depletion is seen when CD47$^+$ cancer cells are treated with a CD47 blockade drug, such as a SIRPα-based drug or an anti-CD47 antibody, in combination with an HDAC inhibitor and particularly with romidepsin and related compounds. The two drugs cooperate in their effects on cancer cells, and cause the depletion of more cancer cells than can be accounted for by their individual effects. In related terms, the HDAC inhibitor is effective to enhance the anti-cancer activity of the CD47 blockade drug.

In one aspect, there is provided a method for treating a subject presenting with CD47$^+$ disease cells, comprising administering a combination comprising a CD47-binding form of SIRPα and an HDAC inhibitor, such as romidepsin.

In a related aspect, there is provided the use of a CD47 blockade drug, such as a SIRPα-based drug, in combination with an HDAC inhibitor for the treatment of a subject presenting with CD47$^+$ disease cells such as cancer.

In another aspect there is provided a pharmaceutical combination comprising a CD47 blockade drug and HDAC inhibitor for use in the treatment of CD47$^+$ disease cells.

There is also provided, in another aspect, a kit comprising a pharmaceutical combination comprising a CD47 blockade drug, such as a soluble SIRPα-based drug, and an HDAC inhibitor, together with instructions teaching their use in the treatment method herein described of CD47$^+$ disease cells.

In a specific embodiment, the combination of the CD47 blockade drug and HDAC inhibitor is for use in the treatment of cancer, including a blood cancer such as a myeloma, a lymphoma or a leukemia.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF REFERENCE TO THE DRAWINGS

FIG. 1 shows results when the multiple myeloma cell lines MM1s and H929 are cultured in the presence of the HDAC inhibitor Romidepsin (at 1, 5 or 10 nM) for 48 hours. Cells are then washed; macrophages and SIRPαFc [TTI-621] (at 1, 5 or 100 nM) or Control Fc are added and the mixture is then subjected to the phagocytosis assay described below. As shown in FIG. 1, culturing MM1s (A) and H929 (B) in Romidepsin for 48 hours results increased SIRPαFc-mediated phagocytosis.

Figure 2:
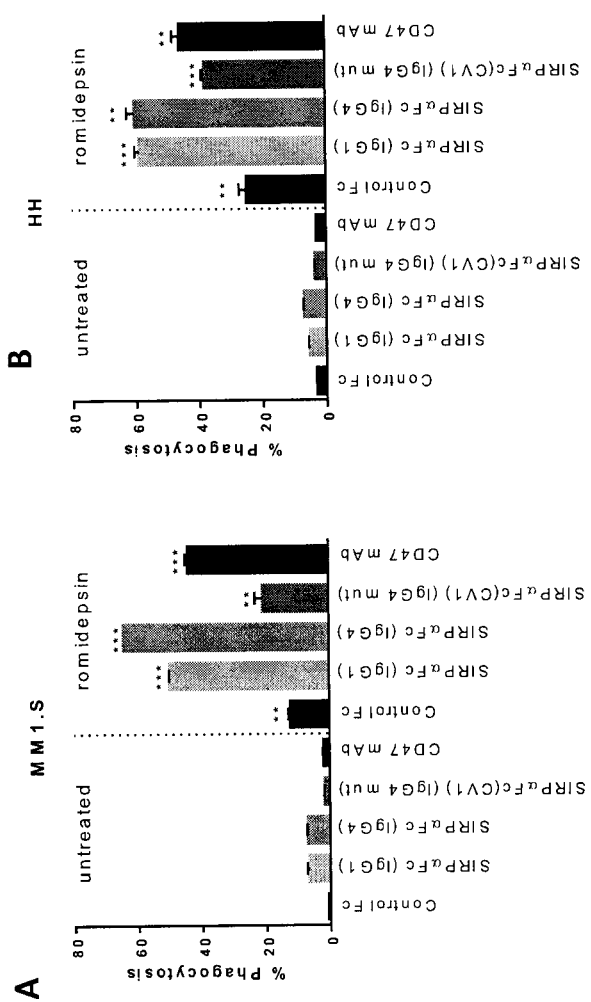

FIG. 2 shows additional results when the multiple myeloma cell lines MM1.S and the cutaneous T-cell lymphoma line HH are cultured in the presence of the HDAC inhibitor Romidepsin (10 nM) for 48 hours. Cells are then washed; macrophages and 100 nM SIRPαFc (IgG1), SIRPαFc (IgG4), SIRPαFc (CV1) (IgG4 mut), CD47 monoclonal antibody (mAb) or Control Fc are added and the mixture is then subjected to the phagocytosis assay described herein. As shown in FIG. 2, culturing MM1.S (A) and HH (B) in Romidepsin for 48 hours results in increased phagocytosis mediated by a variety of CD47 blockade drugs.

DETAILED DESCRIPTION

The present disclosure provides methods, uses, combinations and kits useful for treating subjects that present with disease cells that have a CD47+ phenotype. In this method, subjects receive a combination of a CD47 blockade drug which preferably is a CD47-binding form of SIRPα, and a histone deacetylase (HDAC) inhibitor. The effect of this combination is superior to the effects of either agent alone. This is a statistically significant effect, or benefit, that results particularly when the CD47 blockade drug is a CD47-binding SIRPαFc-based agent. The effect is also seen when the CD47 blockade drug is a CD47-binding antibody. The effect is pronounced when the CD47+ disease cells are CD47+ cancer cells and tumours.

In one aspect, there is provided a method for treating a subject with CD47+ disease cells, comprising administering an effective amount of a drug combination comprising a CD47 blockade drug and a HDAC inhibitor.

In a related aspect, there is provided a use of a CD47 blockade drug in combination with a HDAC inhibitor for the treatment of a subject with CD47+ disease cells.

In another aspect, there is provided a combination comprising a CD47 blockade drug and HDAC inhibitor for use in the treatment of a CD47+ disease.

In a further aspect, there is provided a kit comprising a combination comprising a CD47 blockade drug and HDAC inhibitor together with instructions for the use in the treatment of CD47+ disease cells.

The term CD47+ disease cells means cells having the phenotype CD47+ and are associated with a disease. Cells that are CD47+ can be identified using the methods disclosed herein. In one embodiment, the CD47+ disease cells are cancer cells.

As used herein, a CD47 blockade drug is a drug or agent that interferes with and dampens or blocks signal transmission that results when CD47 interacts with macrophage-presented SIRPα. Also included are CD47-binding agents that block interaction between SIRPα and CD47. CD47-binding forms of human SIRPα are the preferred CD47 blockade drugs for use in the combination herein disclosed. These drugs are based on the CD47-binding extracellular region of human SIRPα. They comprise at least a part of the extracellular region sufficient to confer effective CD47 binding affinity and specificity. So-called "soluble" forms of SIRPα, lacking the membrane anchoring component, are useful and are described in the literature and include those referenced in Novartis' WO 2010/070047, and Stanford's WO2013/109752, and Trillium Therapeutics' WO2014/094122. The CD47 blockade drug can also be a bispecific Fc fusion protein that includes a CD47 binding site.

In a preferred embodiment, the soluble form of SIRPα is an Fc fusion. More particularly, the CD47 blockade drug suitably comprises a CD47-binding part of the human SIRPα protein, in a form fused directly, or indirectly, with an antibody constant region, or Fc (fragment crystallisable) Unless otherwise stated, the term "human SIRPα" as used herein refers to a wild type, endogenous, mature form of human SIRPα. In humans, the SIRPα protein is found in two major forms. One form, the variant 1 or V1 form, has the amino acid sequence set out as NCBI RefSeq NP 542970.1 (residues 27-504 constitute the mature form). Another form, the variant 2 or V2 form, differs by 13 amino acids and has the amino acid sequence set out in GenBank as CAA71403.1 (residues 30-504 constitute the mature form). These two forms of SIRPα constitute about 80% of the forms of SIRPα present in humans, and both are embraced herein by the term "human SIRPα". Also embraced by the term "human SIRPα" are the minor forms thereof that are endogenous to humans and have the same property of triggering signal transduction through CD47 upon binding thereto. The present disclosure is directed most particularly to the drug combinations that include the human SIRP variant 2 form, or V2.

In the present drug combination, useful SIRPαFc fusion proteins comprise one, such as only one, of the three so-called immunoglobulin (Ig) domains that lie within the extracellular region of human SIRPα. More particularly, the present SIRPαFc proteins incorporate at least residues 32-137 of human SIRPα (a 106-mer), which constitute and define the IgV domain of the V2 form according to current nomenclature. This SIRPα sequence, shown below, is referenced herein as SEQ ID No.1.

[SEQ ID No. 1]
EELQVIQPDKSVSVAAGESAILHCTVTSLIPVGPIQWFRGAGPAREL

IYNQKEGHFPRVTTVSESTKRENMDFSISISNITPADAGTYYCVKFR

KGSPDTEFKSGA

In a preferred embodiment, the SIRPαFc fusion proteins incorporate the IgV domain as defined by SEQ ID No.1, and additional, flanking residues contiguous within the SIRPα sequence. This preferred form of the IgV domain, represented by residues 31-148 of the V2 form of human SIRPα, is a 118-mer having SEQ ID No. 2 shown below:

[SEQ ID No. 2]
EEELQVIQPDKSVSVAAGESAILHCTVTSLIPVGPIQWFRGAGPARE

LIYNQKEGHFPRVTTVSESTKRENMDFSISISNITPADAGTYYCVKF

RKGSPDTEFKSGAGTELSVRAKPS

Desirable SIRPα fusion proteins incorporate an Fc region that preferably also has effector function. Fc refers to "fragment crystallisable" and represents the constant region of an antibody comprised principally of the heavy chain constant region and components within the hinge region. An Fc component "having effector function" is an Fc component having at least some natural or engineered function, such as at least some contribution to antibody-dependent cellular cytotoxicity or some ability to fix complement. Also, the Fc will at least bind to Fc receptors. These properties can be revealed using assays established for this purpose. Functional assays include the standard chromium release assay that detects target cell lysis. By this definition, an Fc region that is wild type IgG1 or IgG4 has effector function, whereas the Fc region of a human IgG4 mutated to alter effector function, such as by incorporation of an alteration series that includes Pro233, Val234, Ala235 and deletion of Gly236 (EU), is considered not to have effector function. In a preferred embodiment, the Fc is based on human antibodies of the IgG1 isotype. The Fc region of these antibodies will be readily identifiable to those skilled in the art. In embodiments, the Fc region includes the lower hinge-CH2-CH3 domains.

In a specific embodiment, the Fc region is based on the amino acid sequence of a human IgG1 set out as P01857 in UniProtKB/Swiss-Prot, residues 104-330, and has the amino acid sequence shown below and referenced herein as SEQ ID No.3:

[SEQ ID No. 3]
DKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWL

NGKEYKCKVSNKALPAPIEKTISKAKGQPREPQVYTLPPSRDELTKN

QVSLTCLVKGFYPSDIAVEWESNGQPENNYKTTPPVLDSDGSFFLYS

KLTVDKSRWQQGNVFSCSVMHEALHNHYTQKSLSLSPGK*

Thus, in embodiments, the Fc region has either a wild type or consensus sequence of an IgG1 constant region. In alternative embodiments, the Fc region incorporated in the fusion protein is derived from any IgG1 antibody having a typical effector-active constant region. The sequences of such Fc regions can correspond, for example, with the Fc regions of any of the following IgG1 sequences (all referenced from GenBank), for example: BAG65283 (residues 242-473), BAC04226.1 (residues 247-478), BAC05014.1 (residues 240-471), CAC20454.1 (residues 99-320), BAC05016.1 (residues 238-469), BAC85350.1 (residues 243-474), BAC85529.1 (residues 244-475), and BAC85429.1 (residues (238-469).

In the alternative, the Fc region can be a wild type or consensus sequence of an IgG2 or IgG3 sequence, examples thereof being shown below:
a human IgG2, for example:

(SEQ ID No. 4)
APPVAGPSVFLFPPKPKDTLMISRTPEVTCVVVDVSHEDPEVQFNWY

VDGVEVHNAKTKPREEQFNSTFRVVSVLTVVHQDWLNGKEYKCKVSN

KGLPAPIEKTISKTKGQPREPQVYTLPPSREEMTKNQVSLTCLVKGF

YPSDISVEWESNGQPENNYKTTPPMLDSDGSFFLYSKLTVDKSRWQQ

GNVFSCSVMHEALHNHYTQKSLSLSPGK, as comprised in P01859 of the UniProtKB/Swiss-Prot database;
a human IgG3, for example:

(SEQ ID No. 5)
APELLGGPSVFLFPPKPKDTLMISRTPEVTCVVVDVSHEDPEVQFKW

YVDGVEVHNAKTKPREEQYNSTFRVVSVLTVLHQDWLNGKEYKCKVS

NKALPAPIEKTISKTKGQPREPQVYTLPPSREEMTKNQVSLTCLVKG

FYPSDIAVEWESSGQPENNYNTTPPMLDSDGSFFLYSKLTVDKSRWQ

QGNIFSCSVMHEALHNRFTQKSLSLSPGK, as comprised in P01860 of the UniProtKB/Swiss-Prot database.

In other embodiments, the Fc region has a sequence of a wild type human IgG4 constant region. In alternative embodiments, the Fc region incorporated in the fusion protein is derived from any IgG4 antibody having a constant region with effector activity that is present but, naturally, is significantly less potent than the IgG1 Fc region. The sequences of such Fc regions can correspond, for example, with the Fc regions of any of the following IgG4 sequences: P01861 (residues 99-327) from UniProtKB/Swiss-Prot and CAC20457.1 (residues 99-327) from GenBank.

In a specific embodiment, the Fc region is based on the amino acid sequence of a human IgG4 set out as P01861 in UniProtKB/Swiss-Prot, residues 99-327, and has the amino acid sequence shown below and referenced herein as SEQ ID No.6:

[SEQ ID No. 6]
ESKYGPPCPSCPAPEFLGGPSVFLFPPKPKDTLMISRTPEVTCVVVD

VSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMT

KNQVSLTCLVKGFYPSDIAVEWESNGQPENNYKTTPPVLDSDGSFFL

YSRLTVDKSRWQEGNVFSCSVMHEALHNHYTQKSLSLSLGK

In embodiments, the Fc region incorporates one or more alterations, usually not more than about 10, e.g., up to 5 such alterations, including amino acid substitutions that affect certain Fc properties. In one specific and preferred embodiment, the Fc region incorporates an alteration at position 228 (EU numbering), in which the serine at this position is substituted by a proline ($S^{228}P$), thereby to stabilize the disulfide linkage within the Fc dimer. Other alterations within the Fc region can include substitutions that alter glycosylation, such as substitution of $Asn^{297}$ by glycine or alanine; half-life enhancing alterations such as $T^{252}L$, $T^{253}S$, and $T^{256}F$ as taught in U.S. 62/777,375, and many others. Particularly useful are those alterations that enhance Fc properties while remaining silent with respect to conformation, e.g., retaining Fc receptor binding.

In a specific embodiment, and in the case where the Fc component is an IgG4 Fc, the Fc incorporates at least the $S^{228}P$ mutation, and has the amino acid sequence set out below and referenced herein as SEQ ID No. 7:

[SEQ ID No. 7]
ESKYGPPCPPCPAPEFLGGPSVFLFPPKPKDTLMISRTPEVTCVVVD

VSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMT

KNQVSLTCLVKGFYPSDIAVEWESNGQPENNYKTTPPVLDSDGSFFL

YSRLTVDKSRWQEGNVFSCSVMHEALHNHYTQKSLSLSLGK

The CD47 blockade drug used in the combination is thus preferably a SIRP fusion protein useful to inhibit the binding of human SIRPα with human CD47, thereby to inhibit or reduce transmission of the signal mediated via SIRPα-bound CD47, the fusion protein comprising a human SIRPα component and, fused therewith, an Fc component, wherein the SIRPα component comprises or consists of a single IgV domain of human SIRPα V2 and the Fc component is the constant region of a human IgG having effector function.

In one embodiment, the fusion protein comprises a SIRPα component consisting at least of residues 32-137 of the V2 form of wild type human SIRPα, i.e., SEQ ID No.1. In a preferred embodiment, the SIRPα component consists of residues 31-148 of the V2 form of human SIRPα, i.e., SEQ ID No. 2. In another embodiment, the Fc component is the Fc component of the human IgG1 designated P01857, and in a specific embodiment has the amino acid sequence that incorporates the lower hinge-CH2-CH3 region thereof i.e., SEQ ID No.3.

In a preferred embodiment, therefore, the SIRPαFc fusion protein is provided and used in a secreted dimeric fusion form, wherein the fusion protein incorporates a SIRPα component having SEQ ID No.1 and preferably SEQ ID No, 2 and, fused therewith, an Fc region having effector function and having SEQ ID No.3. When the SIRPα component is SEQ ID No. 1, this fusion protein comprises SEQ ID No.8, shown below:

[SEQ ID No. 8]
EEELQVIQPDKSVSVAAGESAILHCTVTSLIPVGPIQWFRGAGPARE

LIYNQKEGHFPRVTTVSESTKRENMDFSISISNITPADAGTYYCVKF

RKGSPDTEFKSGAGTELSVRAKPSDKTHTCPPCPAPELLGGPSVFLF

PPKPKDTLMISRTPEVTCVVVDVSHEDPEVKFNWYVDGVEVHNAKTK

PREEQYNSTYRVVSVLTVLHQDWLNGKEYKCKVSNKALPAPIEKTIS

KAKGQPREPQVYTLPPSRDELTKNQVSLTCLVKGFYPSDIAVEWESN

GQPENNYKTTPPVLDSDGSFFLYSKLTVDKSRWQQGNVFSCSVMHEA

LHNHYTQKSLSLSPGK*

When the SIRPα component is SEQ ID No. 2, this fusion protein comprises SEQ ID No. 9, shown below:

[SEQ ID No. 9]
EEELQVIQPDKSVSVAAGESAILHCTVTSLIPVGPIQWFRGAGPARE

LIYNQKEGHFPRVTTVSESTKRENMDFSISISNITPADAGTYYCVKF

RKGSPDTEFKSGAGTELSVRAKPSDKTHTCPPCPAPELLGGPSVFLF

PPKPKDTLMISRTPEVTCVVVDVSHEDPEVKFNWYVDGVEVHNAKTK

PREEQYNSTYRVVSVLTVLHQDWLNGKEYKCKVSNKALPAPIEKTIS

KAKGQPREPQVYTLPPSRDELTKNQVSLTCLVKGFYPSDIAVEWESN

GQPENNYKTTPPVLDSDGSFFLYSKLTVDKSRWQQGNVFSCSVMHEA

LHNHYTQKSLSLSPGK

In alternative embodiments, the Fc component of the fusion protein is based on an IgG4, and preferably an IgG4 that incorporates the $S^{228}P$ mutation. In the case where the fusion protein incorporates the preferred SIRPα IgV domain of SEQ ID No.2, the resulting IgG4-based SIRPα-Fc protein has SEQ ID No. 10, shown below:

[SEQ ID No. 10]
EEELQVIQPDKSVSVAAGESAILHCTVTSLIPVGPIQWFRGAGPARE

LIYNQKEGHFPRVTTVSESTKRENMDFSISISNITPADAGTYYCVKF

RKGSPDTEFKSGAGTELSVRAKPSESKYGPPCPPCPAPEFLGGPSVF

LFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKT

ISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMH

EALHNHYTQKSLSLSLGK

In preferred embodiment, the fusion protein comprises, as the SIRPα IgV domain of the fusion protein, a sequence that has/comprises SEQ ID No.2. A preferred SIRPαFc is SEQ ID No.9. Another preferred SIRPαFc has/comprises SEQ ID No.10. The SIRPα sequence incorporated within the CD47 blockade drug can be varied, as described in the literature. That is, useful substitutions within SIRPα include one or more of the following: $L^4V/I$, $V^6I/L$, $A^{21}V$, $V^{27}I/L$, $^{131}T/S/F$, $E^{47}V/L$, $K^{53}R$, $E^{54}Q$, $H^{56}P/R$, $S^{66}T/G$, $K^{68}R$, $V^{92}I$, $F^{94}V/L$, $V^{63}I$, and/or $F^{103}V$. In embodiments, these variants can incorporate a set of amino acid substitutions, such as $V^6I+V^{27}I+I^{31}$ $F+E^{47}V+K^{53}R+E^{54}Q+H^{56}P+S^{66}T+V^{92}I$. CD47-binding SIRPα variants of this type can be used either per se or as Fc fusions.

In embodiments, the CD47 blockade drug is a variant of human SIRPα having higher binding affinity for human CD47 than wild type SIRPα. In a specific embodiment, the variant SIRPα has the sequence shown in SEQ ID No. 11:

[SEQ ID No. 11]
EEELQIIQPDKSVSVAAGESAILHCTITSLFPVGPIQWFRGAGPARV

LIYNQRQGPFPRVTTVSETTKRENMDFSISISNITPADAGTYYCIKF

RKGSPDTEFKSGAGTELSVRAKP

This SIRPα variant comprises the following amino acid substitutions relative to wild type SIRPα: $V^6I+V^{27}I+I^{31}$ $F+E^{47}V+K^{53}R+E^{54}Q+H^{56}P+S^{66}T+V^{92}I$. In a specific embodiment, this variant SIRPα sequence can be fused with a mutated IgG4 Fc region including a Ser228Pro (EU) having virtually no effector function, to yield a CD47 blockade drug having the sequence shown in SEQ ID No. 12:

[SEQ ID No. 12]
EEELQIIQPDKSVSVAAGESAILHCTITSLFPVGPIQWFRGAGPARV

LIYNQRQGPFPRVTTVSETTKRENMDFSISISNITPADAGTYYCIKF

RKGSPDTEFKSGAGTELSVRAKPSESKYGPPCPPCPAPPVAGPSVFL

FPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTI

SKAKGQPREPQVYTLPPSQEEMTKNQVSLTCLVKGFYPSDIAVEWES

NGQPENNYKTTPPVLDSDGSFFLYSRLTVDKSRWQEGNVFSCSVMHE

ALHNHYTQKSLSLSLGK*

Still other types of CD47 blockade drugs can be used in the present method and combination, instead of or in addition to the SIRPα-based drugs. These other drugs include particularly the CD47 antibodies, which bind to CD47 and antagonize the interaction with SIRPα. By blocking that interaction, and because of the Fc region of the antibody, the effect of the CD47 antibodies can be similar to the effect of the SIRPα-based Fc fusion drugs. Examples of CD47 antibodies are described in the literature such as Chugai's US2008/0107654; Stanford's WO2009/091601; InhibRx WO2013/119714, Celgene's WO2016/109415; and Janssen's WO2016/081423. Because these antibodies bind red blood cells, a dosing regimen that takes this into account has been developed and is described in WO2014/149477. The properties of a useful antibody include simply the ability to bind to CD47 in a way that ultimately inhibits signaling by SIRPα, i.e., as an antagonist.

In one embodiment, the CD47 blockade drug is an anti-CD47 antibody that is a chimeric, humanized, human or otherwise recombinant, monoclonal or polyclonal antibody based on the sequence of antibody B6H12 known from the literature and including the sequences:

Amino acid sequence of B6H12 heavy chain variable region

[SEQ ID No. 13]
EVQLVESGGDLVKPGGSLKLSCAASGFTFSGYGMSWVRQTPDKRLEW

VATITSGGTYTYYPDSVKGRFTISRDNAKNTLYLQIDSLKSEDTAIY

FCARSLAGNAMDYWGQGTSVTVSS

Amino acid sequence of B6H12 light chain variable region

[SEQ ID No. 14]
DIVMTQSPATLSVTPGDRVSLSCRASQTISDYLHWYQQKSHESPRLL

IKFASQSISGIPSRFSGSGSGSDFTLSINSVEPEDVGVYYCQNGHGF

PRTFGGGTKLEIK

A full sequence for this antibody and the CDR sequences therein, are available from FIG. 1 in US21030142786, the entire contents of which are incorporated herein by reference.

Other CD47 blockade drugs include CD47Fc proteins, as taught by Viral Logic in WO2010/083253 and by Stanford in U.S. Pat. No. 8,377,448), as well as SIRPα antibodies, as described in UHN's WO2013/056352, Stanford's WO2016/022971, Eberhard's U.S. Pat. No. 6,913,894, and elsewhere. These particular CD47 blockade drugs are not ideal, because they bind to the SIRPα which is presented by most cells in the body. CD47 on the other hand is presented only on macrophages and on a limited variety of other cell types, thus limiting the effects of CD47 binding agents to those cells and tissues.

In a SIRPαFc fusion protein, the SIRPα component and the Fc component are fused, either directly or indirectly, to provide a single chain polypeptide that is ultimately produced as a dimer in which the single chain polypeptides are coupled through intrachain disulfide bonds formed within the Fc region. The nature of the fusing region is not critical. The fusion may be direct between the two components, with the SIRP component constituting the N-terminal end of the fusion and the Fc component constituting the C-terminal end. Alternatively, the fusion may be indirect, through a linker comprised of one or more amino acids, desirably genetically encoded amino acids, such as two, three, four, five, six, seven, eight, nine or ten amino acids, or any number of amino acids between 5 and 100 amino acids, such as between 5 and 50, 5 and 30 or 5 and 20 amino acids. A linker may comprise a peptide that is encoded by DNA constituting a restriction site, such as a BamHI, ClaI, EcoRI, HindIII, PstI, SalI and XhoI site and the like.

The linker amino acids typically and desirably have some flexibility to allow the Fc and the SIRP components to adopt their active conformations. Residues that allow for such flexibility typically are Gly, Asn and Ser, so that virtually any combination of these residues (and particularly Gly and Ser) within a linker is likely to provide the desired linking effect. In one example, such a linker is based on the so-called G4S sequence (Gly-Gly-Gly-Gly-Ser) (SEQ ID No. 15) which may repeat as (G4S)$_n$ where n is 1, 2, 3 or more, or is based on (Gly)n, (Ser)n, (Ser-Gly)n or (Gly-Ser)n and the like. In another embodiment, the linker is GTELSVRAKPS (SEQ ID No.16). This sequence constitutes SIRPα sequence that C-terminally flanks the IgV domain (it being understood that this flanking sequence could be considered either a linker or a different form of the IgV domain when coupled with the IgV minimal sequence described above). It is necessary only that the fusing region or linker permits the components to adopt their active conformations, and this can be achieved by any form of linker useful in the art.

As noted, the CD47 blockade drug such as a SIRPαFc fusion is useful to inhibit interaction between SIRPα and CD47, thereby to block signalling across this axis. Stimulation of SIRPα on macrophages by CD47 is known to inhibit macrophage-mediated phagocytosis by deactivating myosin-II and the contractile cytoskeletal activity involved in pulling a target into a macrophage. Activation of this cascade is therefore important for the survival of CD47$^+$ disease cells, and blocking this pathway enables macrophages to eradicate or at least reduce the CD47$^+$ disease cell population.

The term "CD47$^+$" is used with reference to the phenotype of cells targeted for binding by the present CD47 blockade drugs. Cells that are CD47$^+$ can be identified by flow cytometry using CD47 antibody as the affinity ligand. CD47 antibodies that are labeled appropriately are available commercially for this use (for example, the antibody product of clone B6H12 is available from BD Biosciences). The cells examined for CD47 phenotype can include standard tumour biopsy samples including particularly blood samples taken from the subject suspected of harbouring endogenous CD47$^+$ cancer cells. CD47 disease cells of particular interest as targets for therapy with the present drug combination are those that "over-express" CD47. These CD47$^+$ cells typically are disease cells, and present CD47 at a density on their surface that exceeds the normal CD47 density for a cell of a given type. CD47 overexpression will vary across different cell types, but is meant herein to refer to any CD47 level that is determined, for instance by flow cytometry or by immunostaining or by gene expression analysis or the like, to be greater than the level measurable on a counterpart cell having a CD47 phenotype that is normal for that cell type.

The present drug combination comprises both a CD47 blockade drug that preferably comprises a soluble form of a SIRPα-based drug, as just described, and an inhibitor of histone deacetylase.

Histone deacetylases (HDACs) are a group of enzymes that facilitates the removal of acetyl groups (deacetylation) from lysine residues on histone and non-histone proteins. HDACs regulate chromatin structure and transcription by erasing acetyl groups on histones. Deacetylation of non-histone proteins regulates a range of cellular processes. Human have 18 known HDACs divided in to 4 classes (Class I, II, III and IV).

HDAC inhibitors interfere with the deacetylation process, by inhibiting the enzyme activity of HDACs. These have been described as "epigenetic modifiers" because of their regulation of post-translational modifications. The anti-tumor mechanisms of HDACi are not fully understood, but have been shown to affect a wide range of cellular processes, for example leading to the induction of cell death, cell cycle arrest, and differentiation and inhibition of invasion and migration. HDAC inhibitors are divided into at least four structural classes: hydroxamates, cyclic peptides (depsipeptides), aliphatic acids and benzamides. The selectivity of the compounds varies. Pan-HDACi (non-selective), class-selective and isotype selective inhibitors have been described, resulting in different, often non-redundant anti-tumor effects and target specificity.

In embodiments, the HDAC inhibitor used in the drug combination is a depsipeptide. These are non-ribosomal peptides cyclized via an ester bond. They can contain non-protein amino acids. They include the cyclotetrapeptides that include apicidin and romidepsin, as well as Spiruchostatin A, etamycin, papuamide, neamphamide A, callipeltin A and mirabamides A-D. In particular embodiments, the HDAC inhibitor used in the pharmaceutical combination is a depsipeptide that inhibits the enzymatic activity of HDACs belonging to Class I, such as HDAC1, HDAC2, HDAC3 and HDAC8. These In a preferred embodiment, the HDAC inhibitor in the present combination is romidepsin, a depsipeptide that is a potent inhibitor of Class I HDACs, having the structure shown below:

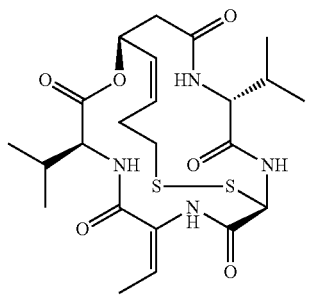 [SMILES: C/C=C1/NC(=O)[C@@H]2NC(=O)[C@@H](C(C)C)NC(=O)C[C@@H](/C=C\CCSS2)OC(=O)[C@H](C(C)C)NC1=O]

Other HDAC inhibitors include compounds such as those listed below in Table 1:

of T cell lymphoma including peripheral and cutaneous, and can be used for this purpose when combined with CD47 blockade drug.

Each drug included in the combination can be formulated separately for use in combination. The drugs are said to be used "in combination" when, in a recipient of both drugs, the effect of one drug enhances or at least influences the effect of the other drug.

The two drugs in the combination cooperate to provide an effect on target $CD47^+$ cells that is greater than the effect of either drug alone. This benefit manifests as a statistically significant improvement in a given parameter of target cell fitness or vitality. For instance, a benefit in $CD47^+$ cancer cells, when exposed to a combination of CD47 blockade drug and HDAC inhibitor, could be a statistically significant decrease in the number of living cancer cells (hence a depletion), relative to non-treatment, or a decrease in the number or size of cancer cells or tumours, or an improvement in the endogenous location or distribution of any particular tumour type. In embodiments, the improvement resulting from treatment with the drug combination can manifest as an effect that is at least additive and desirably synergistic, relative to results obtained when only a single agent or an agent combination is used.

In use, each drug in the combination can be formulated as it would be for monotherapy, in terms of dosage size and form and regimen. In this regard, the improvement resulting

TABLE 1

| Compound | Class | Compound | Class |
| --- | --- | --- | --- |
| Romidepsin (Istodax ®) | depsipeptide | Trapoxin B | cyclic tetrapeptide |
| Spiruchostatin A | depsipeptide | Apicidin | Cyclic peptide |
| etamycin | depsipeptide | Valproic acid Mg | Aliphatic acid |
| Trichostatin A | hydroxamate | Mocetinostat | benzamide |
| Belinostat (Beleodaq ®) | hydroxamate | CI994 | benzamide |
| Panobinostat (Farydak ®) | hydroxamate | Entinostat | benzamide |
| Dacinostat (LAQ824) | hydroxamate | HBI-8000 | benzamide |
| Rocilinostat (ACY-1215) | hydroxamate | 4SC-202 | benzamide |
| Abexinostat (PCI24781) | hydroxamate | chidamide | Benzamide |
| Pracinostat (SB939) | hydroxamate | sulforaphane | |
| Resminostat (4SC-201) | hydroxamate | trasquinimod | |
| Givinostat (ITF2357) | hydroxamate | NCH51 | |
| Quisinostat (JNJ-26481585) | hydroxamate | KD 5170 | |
| CUDC-101 | hydroxamate | RG2833 | |
| AR-42 (HDAC-42) | hydroxamate | diaminozide | |
| CHR-2845, CHR-3996 | hydroxamate | CHAPS | |
| SB939 | hydroxamate | parthenolide | |
| M344 | hydroxamate | apistatin | |
| tubacin | hydroxamate | Tubastatin A | |
| | | Tacediniline | |
| | | Kevetrin | |
| | | Sirtuin family | |

In a specific embodiment of the present method, the CD47 blockade drug is used in combination with romidepsin. As noted, romidepsin is marketed under the trademark Istodax® and is provided as a lyophilized powder for intravenous injection. It is supplied as a kit which includes a sterile, lyophilized powder in a single-use vial containing 10 mg of romidepsin and 20 mg of carrier, povidone. Each kit also provides one sterile vial containing 2 mL of diluent (80% propylene glycol, and 20% dehydrated alcohol), for reconstitution in 0.9% saline. Established dosing is 14 mg/m2 with intravenous administrations on days 1, 8 and 15 of a 28 day cycle. It can be used in this same manner for purposes of the present disclosure, although cooperation with the CD47 blockade drug should permit the use of a reduced romidepsin dose or dosing frequency. It is used particularly for the treatment of blood cancers such as forms from their combined use may permit the use of somewhat reduced dosage sizes or frequencies, as would be revealed in an appropriately controlled clinical trial.

The mechanism by which an HDAC inhibitor contributes to the activity of a CD47 blockade drug, in the present combination, is not known. The HDAC inhibitors likely have a direct activity on some tumour cells, and preliminary data suggest that treatment of tumor cells with these inhibitors results in upregulation of pro-phagocytic ("eat-me") signals on the surface of some tumor cells.

In this approach, each drug is provided in a dosage form comprising a pharmaceutically acceptable carrier, and in a therapeutically effective amount. As used herein, "pharmaceutically acceptable carrier" means any and all solvents, dispersion media, coatings, antibacterial and antifungal agents, isotonic and absorption delaying agents, and the like that are physiologically compatible and useful in the art of protein/antibody formulation. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent. Each of the CD47 blockade drug, e.g., SIRPαFc fusion protein, and the HDAC inhibitor is formulated using practices standard in the art of therapeutics formulation. Solutions that are suitable for intravenous administration, such as by injection or infusion, are particularly useful. The HDAC inhibitor will of course be formulated as permitted by the regulatory agencies when it is a drug approved for use in humans.

Sterile solutions can be prepared by incorporating the active compound in the required amount in an appropriate solvent with one or a combination of ingredients noted above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation are vacuum drying and freeze-drying (lyophilization) that yield a powder of the active ingredient plus any additional desired ingredient from a previously sterile-filtered solution thereof.

As used herein, "effective amount" refers to an amount effective, at dosages and for a particular period of time necessary, to achieve the desired therapeutic result. A therapeutically effective amount of each drug in the combination may vary according to factors such as the disease state, age, sex, and weight of the individual, and the ability of the drug to elicit a desired response in the recipient. A therapeutically effective amount is also one in which any toxic or detrimental effects of the pharmacological agent are outweighed by the therapeutically beneficial effects. The HDAC inhibitor will of course be formulated in amounts that are suitable for patient dosing, as permitted by the regulatory agencies that have approved its use in humans. In use, each drug in the combination thus is formulated as it would be for monotherapy, in terms of dosage size and form and regimen. In this regard, the cooperation/benefit resulting from their combined use may permit the use of somewhat reduced dosage sizes or frequencies, as would be revealed in an appropriately controlled clinical trial.

The SIRPαFc fusion protein can be administered to the subject through any of the routes established for protein delivery, in particular intravenous, intradermal, intratumoural and subcutaneous injection or infusion, or by oral or nasal administration.

The drugs in the present combination can be administered sequentially or, essentially at the same time. In embodiments, the HDAC inhibitor is given before administration of the CD47 blockade drug, e.g., SIRPαFc. In the alternative, the HDAC inhibitor can be given after or during administration of the CD47 blockade drug, e.g., SIRPαFc. Thus, in embodiments, the subject undergoing therapy is a subject already treated with one of the combination drugs, such as the HDAC inhibitor, that is then treated with the other of the combination drugs, such as the CD47 blockade drug.

Dosing regimens are adjusted to provide the optimum desired response (e.g., a therapeutic response). For example, a single bolus of each drug may be administered, or several divided doses may be administered over time or the dose may be proportionally reduced or increased as indicated by the therapeutic situation. It is especially advantageous to formulate parenteral compositions in unit dosage form for ease of administration and uniformity of dosage. "Unit dosage form" as used herein refers to physically discrete units suited as unitary dosages for the subjects to be treated; each unit contains a predetermined quantity of active compound calculated to produce the desired therapeutic effect in association with the required pharmaceutical carrier.

The drugs can be formulated in combination, so that the combination can be introduced to the recipient in one administration, e.g., one injection or one infusion bag. Alternatively, the drugs can be combined as separate units that are provided together in a single package, and with instructions for the use thereof according to the present method. In another embodiment, an article of manufacture containing the SIRPαFc drug and HDAC inhibitor combination in an amount useful for the treatment of the disorders described herein is provided. The article of manufacture comprises one or both drugs of the present antibody drug combination, as well as a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or vial having a stopper pierceable by a hypodermic injection needle). The label on or associated with the container indicates that the composition is used in combination with another CD47 blockade drug in accordance with the present disclosure, thereby to elicit a synergistic effect on the CD47$^+$ disease cells. The article of manufacture may further comprise a second container comprising a pharmaceutically-acceptable buffer, such as phosphate-buffered saline, Ringer's solution and dextrose solution. It may further include other matters desirable from a commercial and use standpoint, including other buffers, diluents, filters, needles, syringes, and package inserts with instructions for use.

For administration the dose for the CD47 blockade drug will be within the range from about 0.0001 to 100 mg/kg, and more usually 0.01 to 5 mg/kg, of the host body weight. For example SIRPαFc dosages can be 0.3 mg/kg body weight, 1 mg/kg body weight, 3 mg/kg body weight, 5 mg/kg body weight or 10 mg/kg body weight or within the range of 0.1-100 mg/kg. When the CD47 blockade drug is a SIRPαFc fusion protein of SEQ ID No.9, the dose can be about 1-5 mg per injection, such as intratumoural injection.

The SIRPαFc protein displays negligible binding to red blood cells. There is accordingly no need to account for an RBC "sink" when dosing with the drug combination. Relative to other CD47 blockade drugs that are bound by RBCs, it is estimated that the present SIRPαFc fusion can be effective at doses that are less than half the doses required for drugs that become RBC-bound, such as CD47 antibodies. Moreover, the SIRPα-Fc fusion protein is a dedicated antagonist of the SIRPα-mediated signal, as it displays negligible CD47 agonism when binding thereto. There is accordingly no need, when establishing medically useful unit dosing regimens, to account for any stimulation induced by the drug.

The drug combination is useful to treat a variety of CD47$^+$ disease cells. These include particularly CD47$^+$ cancer cells, including liquid and solid tumours. Solid tumours can be treated with the present drug combination, to reduce the size, number, distribution or growth rate thereof and to control growth of cancer stem cells. Such solid tumours include CD47+ tumours in bladder, brain, breast, lung, colon, ovary, prostate, liver and other tissues as well. In one embodiment, the drug combination can used to inhibit the growth or proliferation of hematological cancers. As used herein, "hematological cancer" refers to a cancer of the blood, and includes leukemia, lymphoma and myeloma among others. "Leukemia" refers to a cancer of the blood, in which too many white blood cells that are ineffective in fighting infection are made, thus crowding out the other parts that make up the blood, such as platelets and red blood cells. It is understood that cases of leukemia are classified as acute or chronic. Certain forms of leukemia may be, by way of example, acute lymphocytic leukemia (ALL); acute myeloid leukemia (AML); chronic lymphocytic leukemia (CLL); chronic myelogenous leukemia (CML); myeloproliferative disorder/neoplasm (MPDS); and myelodysplastic syndrome. "Lymphoma" may refer to a Hodgkin's lymphoma, both indolent and aggressive non-Hodgkin's lymphoma, cutaneous T cell lymphoma (CTCL), Burkitt's lymphoma, Mantle cell lymphoma (MCL) and follicular lymphoma (small cell and large cell), among others. Myelomas include multiple myeloma (MM), giant cell myeloma, heavy-chain myeloma, and light chain myeloma and Bence-Jones myeloma.

In some embodiments, the hematological cancer treated with the drug combination is a CD47+ leukemia, preferably selected from acute lymphocytic leukemia, acute myeloid leukemia, chronic lymphocytic leukemia, chronic myelogenous leukemia, and myelodysplastic syndrome, preferably, human acute myeloid leukemia.

In other embodiments, the hematological cancer treated with the drug combination is a CD47+ lymphoma or myeloma selected from Hodgkin's lymphoma, both indolent and aggressive non-Hodgkin's lymphoma, diffuse large cell lymphoma (DLBCL), mantle cell lymphoma, T cell lymphoma including mycosis fungoides, Sezary's syndrome, Burkitt's lymphoma, follicular lymphoma (small cell and large cell), multiple myeloma (MM), giant cell myeloma, heavy-chain myeloma, and light chain or Bence-Jones myeloma as well as leimyosarcoma.

In a specific embodiment, the cancer treated with the present combination is multiple myeloma. In another specific embodiment, the targeted cancer is mantle cell lymphoma. In a further embodiment, the cancer treated with the present combination is relapsed or refractory Hodgkin's lymphoma. In another specific embodiment, the CD47 blockade drug is SIRPαFc. In a further specific embodiment the HDAC inhibitor is romidepsin.

In still other embodiments, romidepsin is used in combination with SIRPαFc, such as SEQ ID No.9 or SEQ ID No.10, such as for the treatment of cutaneous T cell lymphoma or multiple myeloma. In another embodiment, the combination is used to treat a T cell lymphoma such as mycosis fungoides or Sezary's syndrome.

Thus, in specific embodiments, there is provided the use of a CD47 blockade drug in combination with an HDAC inhibitor for the treatment of a particular CD47+ cancer, wherein:
i) the CD47 blockade drug is SIRPαFc of SEQ ID No.9 and the HDAC inhibitor is romidepsin, such as for the treatment of a cancer that is cutaneous T cell lymphoma or multiple myeloma or relapsed or refractory Hodgkin's lymphoma;
ii) the CD47 blockade drug is SIRPαFc of SEQ ID No.10 and the HDAC inhibitor is romidepsin, such as for the treatment of a cancer that is cutaneous T cell lymphoma or multiple myeloma or relapsed or refractory Hodgkin's lymphoma;
iii) the CD47 blockade drug is anti-CD47 antibody and the HDAC inhibitor is romidepsin, such as for the treatment of a cancer that is cutaneous T cell lymphoma or multiple myeloma.

It will be appreciated that other CD47 blockade drugs can be used in combination with HDAC inhibitors. Desirable combinations will show a statistically significant improvement in cancer cell response. This can be demonstrated as a statistically significant improvement in HDAC inhibitor activity caused by combination with a CD47 blockade drug, or vice versa, where statistical significance is shown as noted in the examples that follow and desirably, provides a p value >0.05 and more desirably >0.01 such as >0.001.

The combination therapy, comprising CD47 blockade and HDAC inhibition can also be exploited together with any other agent or modality useful in the treatment of the targeted indication, such as surgery as in adjuvant therapy, or with additional chemotherapy as in neoadjuvant therapy.

The following non-limiting examples are illustrative of the present disclosure.

EXAMPLES

Heparinized whole blood was obtained from normal healthy human donors (Biological Specialty Corporation) and informed consent was obtained from all donors. Peripheral blood mononuclear cells (PBMCs) were isolated over Ficoll-Paque Plus density gradient (GE Healthcare) and CD14+ monocytes were isolated from PBMCs by positive selection using CD14 antibody-coated MicroBead separation (Miltenyi Biotec). Monocytes were differentiated into macrophages by culturing for seven days in X-Vivo-15 media (Lonza) supplemented with M-CSF (PeproTech). 24 hours prior to the phagocytosis assay, macrophages were primed with IFN-γ (PeproTech). 48 hours prior to the phagocytosis assay, Romidepsin (1, 5 or 10 nM) was added to tumor cells. On the day of the phagocytosis assay, macrophages were co-cultured with a violet proliferation dye 450 (VPD450)-labeled human multiple myeloma cell lines (MM1s or H929) in the presence of 1, 5 or 100 nM human SIRPαFc (V region of human SIRPα variant 2 fused with IgG1 Fc), 100 nM control Fc [human IgG1 Fc region (hinge-CH2-CH3)] for two hours. Phagocytosis was assessed as 30% VPD450+ cells of live, single CD14+ CD11b+ macrophages by flow cytometry. Results shown in FIGS. 1 and 2 are representative of two independent experiments.

Results are shown in FIG. 1 and are duplicates from a single experiment. Results shown in FIG. 2 reveal the effects of a wider array of CD47 blockade drugs used in combination with romidepsin. For FIG. 2, methods were the following:

Macrophages were prepared from human peripheral blood mononuclear cells (PBMCs) obtained from healthy donors (BioreclamationIVT); informed consent was obtained from all donors. CD14+ monocytes were isolated by positive selection using the EasySep® human monocyte isolation kit (Stemcell Technologies). Monocytes were differentiated into macrophages by culturing the cells in X-VIVO 15 media (Lonza) supplemented with human m-CSF (PeproTech) for 10 days. Macrophages were primed with human IFNγ (PeproTech) one day prior to the phagocytosis assay. 48 hours prior to the phagocytosis assay, 10 nM Romidepsin was added to tumor cells. On the day of the phagocytosis assay, macrophages were co-cultured with a violet proliferation dye 450 (VPD450)-labeled human cell lines (MM1.S or HH) in the presence 100 nM human SIRPαFc (IgG1, SEQ ID No.9), SIRPαFc (IgG4, SEQ ID No.10), SIRPαFc (CV1, (IgG4 mut, SEQ ID No. 12), CD47 monoclonal antibody B6H12 (mAb, SEQ ID Nos. 13 and 14) or Control Fc for two hours. Phagocytosis was assessed as % VPD450+ cells of live, single CD14+CD11b+ macrophages by flow cytometry. Statistical significance was calculated by unpaired t-test using GraphPad Prism software comparing untreated vs romidepsin treated cells.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

---

We claim:

1. A method of treating a subject presenting with CD47+ disease cells, the method comprising administering a combination of a CD47 blockade drug and a histone deacetylase (HDAC) inhibitor.

2. The method according to claim 1, wherein the HDAC inhibitor is a depsipeptide.

3. The method according to claim 2, wherein the HDAC inhibitor is romidepsin.

4. The method according to claim 1, wherein the CD47 blockade drug comprises a CD47-binding form of human SIRPα.

5. The method according to claim 4, wherein the CD47-binding form of human SIRPα is a CD47-binding fragment of human SIRPα.

6. The method according to claim 5, wherein the CD47-binding fragment of human SIRPα comprises the V region of human SIRPα.

7. The method according to claim 1, wherein the CD47 blockade drug is an Fc fusion protein comprising the V region of soluble human SIRPα variant 2.

8. The method according to claim 7, wherein the Fc fusion protein comprising soluble SIRPα comprises SEQ ID No. 9.

9. The method according to claim 7, wherein the Fc fusion protein comprising soluble SIRPα comprises SEQ ID No. 10.

10. The method according to claim 1, wherein the CD47 blockade drug comprises soluble SIRPα having one or more amino acid substitutions selected from L4V/I, V6I/L, A21V, V27I/L, I31T/S/F, E47V/L, K53R, E54Q, H56P/R, S66T/G, K68R, V92I, F94V/L, V63I, and F103V.

11. The method according to claim 1, wherein the CD47 blockade drug is an anti-CD47 antibody.

12. The method according to claim 1, wherein the CD47+ disease cells are cancer cells.

13. The method according to claim 12 wherein the cancer cells are blood cancer cells or solid tumour cells.

14. The method according to claim 12, wherein the disease cells are cells of a cancer type selected from acute lymphocytic leukemia (ALL); acute myeloid leukemia (AML); chronic lymphocytic leukemia (CLL); chronic myelogenous leukemia (CML); myeloproliferative disorder/neoplasm (MPDS); and myelodysplastic syndrome.

15. The method according to claim 12, wherein the cancer is a lymphoma selected from a Hodgkin's lymphoma, both indolent and aggressive non-Hodgkin's lymphoma, Burkitt's lymphoma, and follicular lymphoma (small cell and large cell).

16. The method according to claim 12, wherein the cancer is a myeloma selected from multiple myeloma (MM), giant cell myeloma, heavy-chain myeloma, and light chain or Bence-Jones myeloma.

17. The method according to claim 1, wherein the HDAC inhibitor is for use in a subject that has already received the CD47 blockade drug.

* * * * *